United States Patent
Mueller et al.

(10) Patent No.: US 6,776,890 B1
(45) Date of Patent: Aug. 17, 2004

(54) METHODS FOR OPERATING A MIXED POTENTIAL EXHAUST SENSOR AND CIRCUIT CONFIGURATIONS FOR CARRYING OUT SAID METHOD

(75) Inventors: Bernd Mueller, Leonberg (DE); Thomas Brinz, Bissingen unter der Teck (DE); Bernd Schumann, Rutesheim (DE); Bernhard Bloemer, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 137 days.

(21) Appl. No.: 09/856,912
(22) PCT Filed: Sep. 28, 2000
(86) PCT No.: PCT/DE00/03384
§ 371 (c)(1),
(2), (4) Date: Aug. 23, 2001
(87) PCT Pub. No.: WO01/23730
PCT Pub. Date: Apr. 5, 2001

(30) Foreign Application Priority Data

Sep. 30, 1999 (DE) .......................................... 199 47 240

(51) Int. Cl.[7] ............................................ G01N 27/407
(52) U.S. Cl. ........................ 204/406; 204/425; 73/23.31
(58) Field of Search ................................ 204/406, 424, 204/425, 427; 205/781, 783.5, 784, 784.5, 785, 787; 73/23.31

(56) References Cited

U.S. PATENT DOCUMENTS

| | | | |
|---|---|---|---|
| 4,150,562 A | * 4/1979 | Nielsen | ..................... 73/23.21 |
| 4,905,652 A | * 3/1990 | Nakajima et al. | ........... 123/679 |
| 5,344,548 A | 9/1994 | Alberti et al. | |
| 5,630,920 A | 5/1997 | Friese et al. | |
| 6,290,828 B1 | * 9/2001 | Yaguchi | ..................... 204/425 |
| 6,551,497 B1 | * 4/2003 | Gao et al. | .................... 205/781 |

FOREIGN PATENT DOCUMENTS

GB     2119933     11/1983

OTHER PUBLICATIONS

Logothetis et al, "High Temperature Oxygen Sensors Based on Electrochemical Oxygen Pumping", pp. 136–154, Fundamentals and Applications of Chemical Sensors, 1986.*

* cited by examiner

Primary Examiner—Kaj K. Olsen
(74) Attorney, Agent, or Firm—Walter Ottesen

(57) ABSTRACT

A method for operating a mixed-potential exhaust-gas probe for an internal combustion engine having a heatable probe ceramic 1.3 with a first electrode 1.5, which is arranged in a chamber 1.6 and is subjected to the reference atmosphere and with a second electrode 1.4 which detects gas molecules and is arranged in the exhaust gas of the internal combustion engine, a pump voltage being applied between the first and second electrodes by means of a pump voltage source, so that, in the interior of the chamber 1.6, a somewhat reduced oxygen partial pressure is adjusted by the electrochemical pumping off of the oxygen molecules, characterized in that one applies a constant external voltage to the electrodes (1.4, 1.5) with this voltage deviating from the thermodynamic equilibrium voltage of the wanted reaction, measuring and evaluating the current dropping across the electrodes (1.4, 1.5).

4 Claims, 4 Drawing Sheets

(State of the Art)

METHODS FOR OPERATING A MIXED POTENTIAL EXHAUST SENSOR AND CIRCUIT CONFIGURATIONS FOR CARRYING OUT SAID METHOD

FIELD OF THE INVENTION

The invention relates to methods for operating a mixed-potential exhaust-gas probe and circuit arrangements for carrying out these methods.

BACKGROUND OF THE INVENTION

Mixed-potential exhaust-gas probes are utilized, for example, as gas sensors to detect the hydrocarbon concentration of the internal combustion engine or as NOx probes for detecting the nitrogen oxide component in the exhaust gas of internal combustion engines.

These probes are with respect to their configuration similar to the λ-probes and are presented, for example, in the text of Bosch entitled "Kraftfahrtechnisches Taschenbuch", 22nd edition, 1995, starting at page 490.

In known mixed-potential exhaust-gas probes, the signal is measured: as a voltage between two electrodes; via the short-circuit current between the electrodes; or, by tapping the voltage measurable between the electrodes and dropping across a resistor.

SUMMARY OF THE INVENTION

It is an object of the invention to provide a method for operating a mixed-potential exhaust-gas probe wherein a highest possible selectivity is made possible with respect to the individual components of the exhaust gas even in the presence of sometimes very large transverse sensitivities.

Furthermore, it is an object of the invention to provide circuit arrangements which make possible to carry out the methods with a technically simple configuration and the least number of components.

By applying a constant external voltage, the probe can be adjusted to some extent to individual exhaust-gas constituents which are to be detected. The external voltage is different from the thermodynamic equilibrium voltage.

The external constant voltage is determined previously and preferably experimentally.

In this case too, the exhaust-gas probe is adjusted to a certain extent to the detection of individual gas components of the exhaust gas.

The magnitude of the current, which is to be applied to the probe ceramic, is determined experimentally.

The sensitivity of the probe can be considerably increased by the voltage or the current which is distinguished from the thermodynamic equilibrium voltage and the thermodynamic equilibrium current, respectively.

A voltage-polarized current measurement (that is, a measurement of the current which drops on the electrodes of the mixed-potential exhaust-gas probe) at constant external voltage can be realized in a technically very simple manner with an inverting operational amplifier. A voltage divider is connected to the non-inverting input of the operational amplifier and one of the electrodes of the exhaust-gas probes is connected to the inverting input of the operational amplifier. A reference resistor is arranged in the feedback loop of the operational amplifier.

A current polarized voltage measurement is made possible in a technically simple realizable manner with a non-inverting operational amplifier. The voltage measurement is a measurement of the voltage, which adjusts between the electrodes, when applying a constant current to the probe ceramic. A voltage divider is arranged at the non-inverting input of the operational amplifier and a reference resistor is arranged at the inverting input thereof. The exhaust-gas sensor is arranged in the feedback loop of the operational amplifier.

In an advantageous embodiment, switching means are provided via which switching can take place between the two circuit arrangements.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
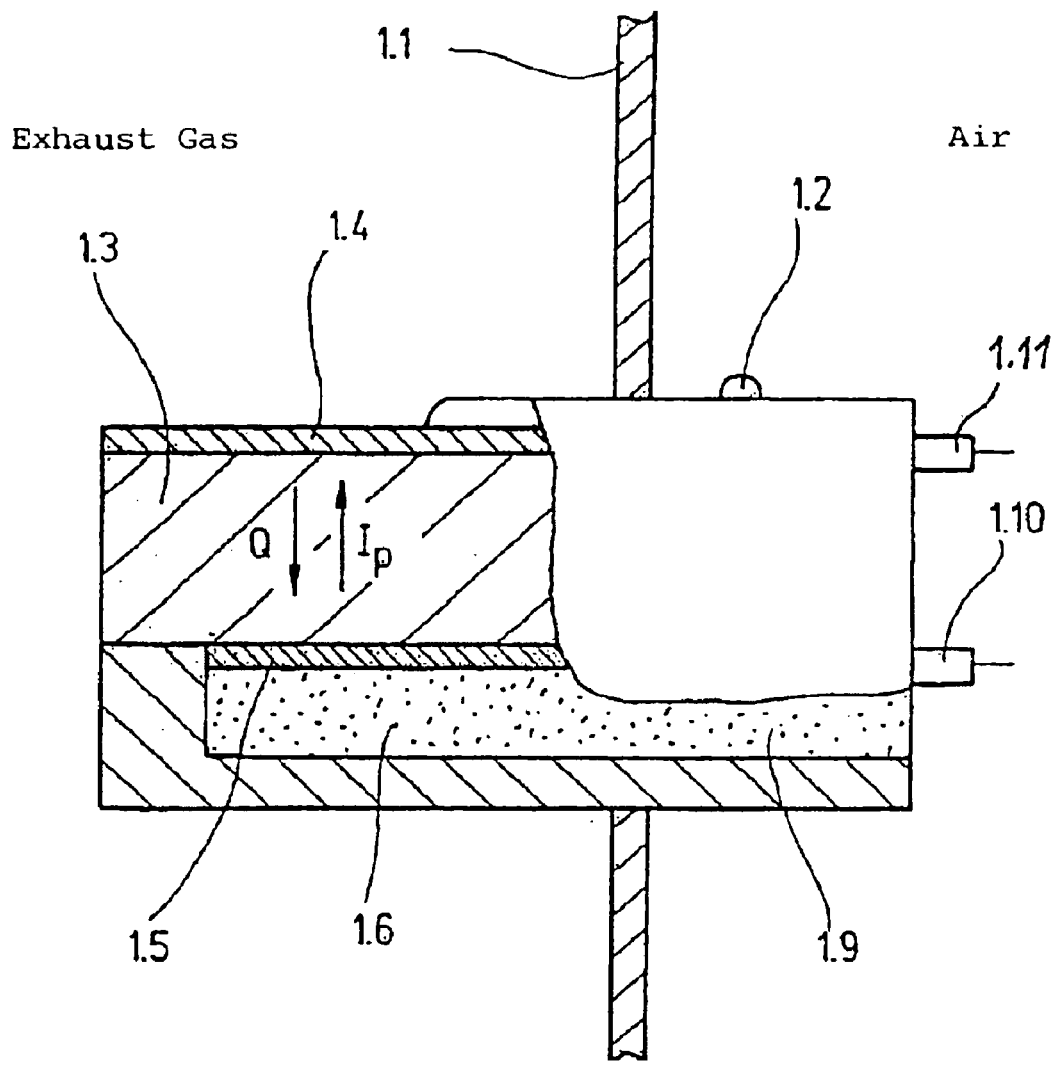
FIG. 1 is an exhaust-gas probe having a pumped reference and known from the state of the art.

FIG. 1 shows, in section, an exhaust-gas probe 1.2 on an exhaust-gas pipe of which a wall 1.1 is shown. This wall 1.1 partitions the exhaust gas of an internal combustion engine (left) from the ambient air (right). The exhaust-gas probe 1.2 includes a solid-state electrolyte 1.3 in its exhaust-gas end portion. The solid-state electrolyte 1.3 is between a first electrode 1.4 subjected to the exhaust gas and a further electrode 1.5. A reference gas volume 1.6 communicates with the electrode 1.5 and is in direct contact with the ambient air via a channel 1.9. The electrode 1.5 is connected to a measuring feedline 1.10 and the electrode 1.4 is connected to a measurement line 1.11.

For maintaining a stable reference atmosphere, it is essential that the supply of oxygen via the pump current $I_p$ exceeds, in time average, the occurring losses of oxygen. Such losses occur perforce during the measurement of a voltage in the electrodes when the voltage measurement is based on a current measurement via a measuring resistor in a manner known per se. Typically, measurement resistors in the megaohm range are used in the range of the measurement of voltages in the order of magnitude of the output voltage of the exhaust-gas probe of 1 V. As a consequence, a measurement current flows in the microampere range. For electrolytes, this current is carried by oxygen ions from the reference volume so that the oxygen concentration in the reference gas volume reduces because of the measurement.

A measurement pulse can be so dimensioned with respect to its height and time duration that it supplies the required pump current in time average.

The basic idea of the invention is to achieve an improvement of the gas selectivity in that a constant external potential or a constant external current is applied to the sensor electrodes (1.4, 1.5). In this way, the signal formation can be adjusted to a certain extent to individual gases and thereby the selectivity can be improved. If a constant external potential, that is, a constant external voltage is applied, which deviates from the thermodynamic equilibrium voltage, the adjusting current is measured and evaluated. If a constant current is applied, then the measurement and evaluation of the potential, which adjusts, or the voltage, which adjusts, takes place.

By applying a voltage which lies above the thermodynamic equilibrium voltage of the disturbing electrode reaction, it is especially possible to influence the course of the disturbing reaction so that no disturbing components participate in the wanted reaction.

Figure 4:
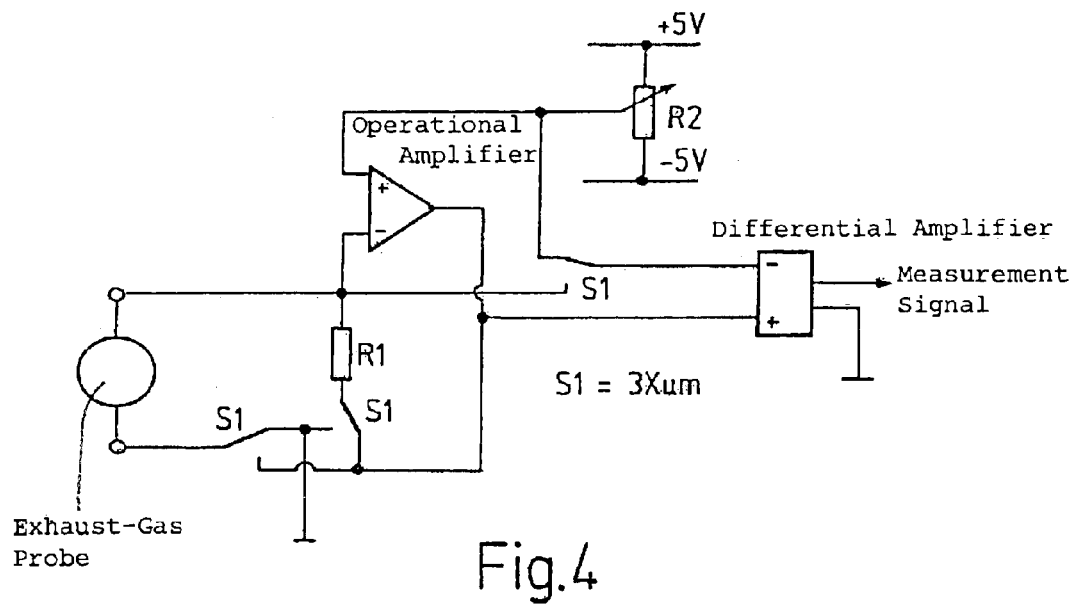
FIG. 4 is an embodiment of a circuit arrangement of the invention for the voltage-polarized current measurement of a mixed potential exhaust-gas probe; and, FIG. 5 shows an embodiment of a circuit arrangement according to the invention for the current-polarized voltage measurement.

FIG. 4 shows an embodiment of a circuit arrangement for the voltage-polarized current measurement wherein one applies a constant external voltage to the electrodes (1.4, 1.5) of the exhaust-gas probe and measures and evaluates the current dropping via the electrodes (1.4, 1.5). The applied voltage deviates from the thermodynamic equilibrium voltage. The circuit includes an operational amplifier having a feedback loop in which a reference resistance R1 is connected; that is, the reference resistance R1 is connected between the inverting input of the operational amplifier and the output thereof. The exhaust-gas probe is connected to ground at the inverting input. A voltage divider identified by R2 is connected to the non-inverting input of the operational amplifier. A differential amplifier is arranged between the non-inverting input and the output and the output signal to ground is the measurement signal. If the internal resistance or the potential at the exhaust-gas probe changes, then the operational amplifier controls the voltage, which is present at the exhaust-gas probe, via the reference resistance R1 which acts as a feedback resistor. The signal between the non-inverting input and the output of the operational amplifier is proportional to the current which flows through the sensor and is amplified by the differential amplifier.

Figure 5:
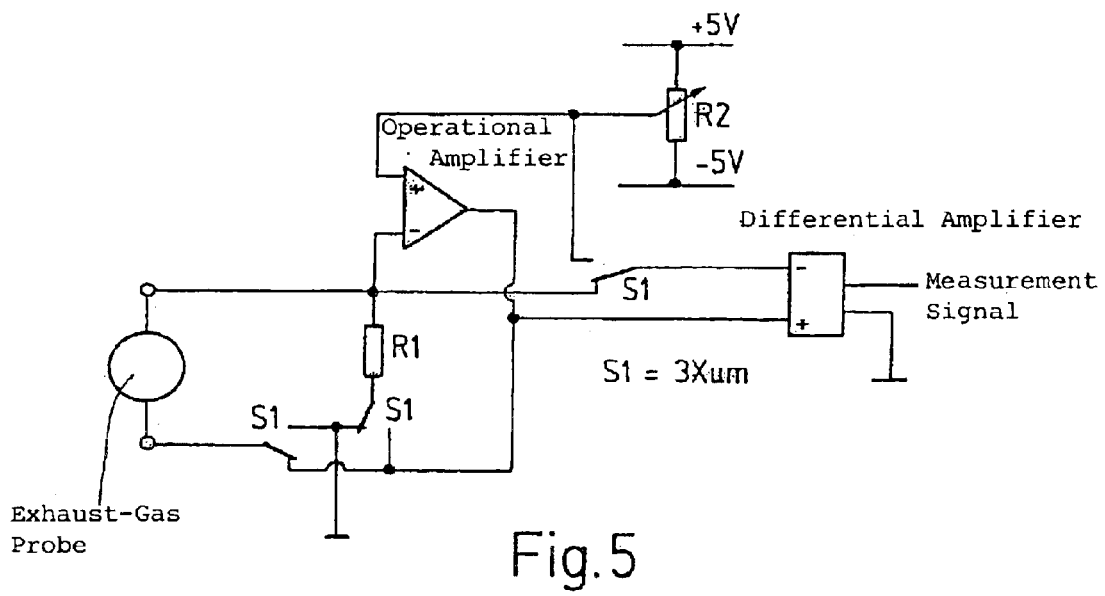

The circuit further includes a three-way switch S1 by means of which switching can take place to the circuit arrangement shown in FIG. 5. The circuit arrangement shown in FIG. 5 defines a current-polarized voltage measurement wherein a constant current can be applied to the probe ceramic and the voltage which adjusts can be measured and evaluated. The circuit arrangement shown in FIG. 5 distinguishes from the circuit arrangement in FIG. 4 in that the reference resistor R1 is connected to the inverting input of the operational amplifier; in contrast, the exhaust-gas probe is arranged in the feedback loop of the operational amplifier. The voltage divider R2 is connected to the non-inverting input. In this case, the differential amplifier amplifies the voltage dropping across-the exhaust-gas probe and this voltage is evaluated as a measurement signal. In this circuit, a current is impressed upon the exhaust-gas probe and this current is determined only by the voltage adjusted via the voltage divider (that is, by means of the potentiometer R2) and the resistor R1. Since the exhaust-gas probe lies in the feedback of the operational amplifier, the internal resistance of the exhaust-gas probe has no influence on the impressed current. The voltage drop across the exhaust-gas probe is measured with the aid of the differential amplifier.

Figure 2:
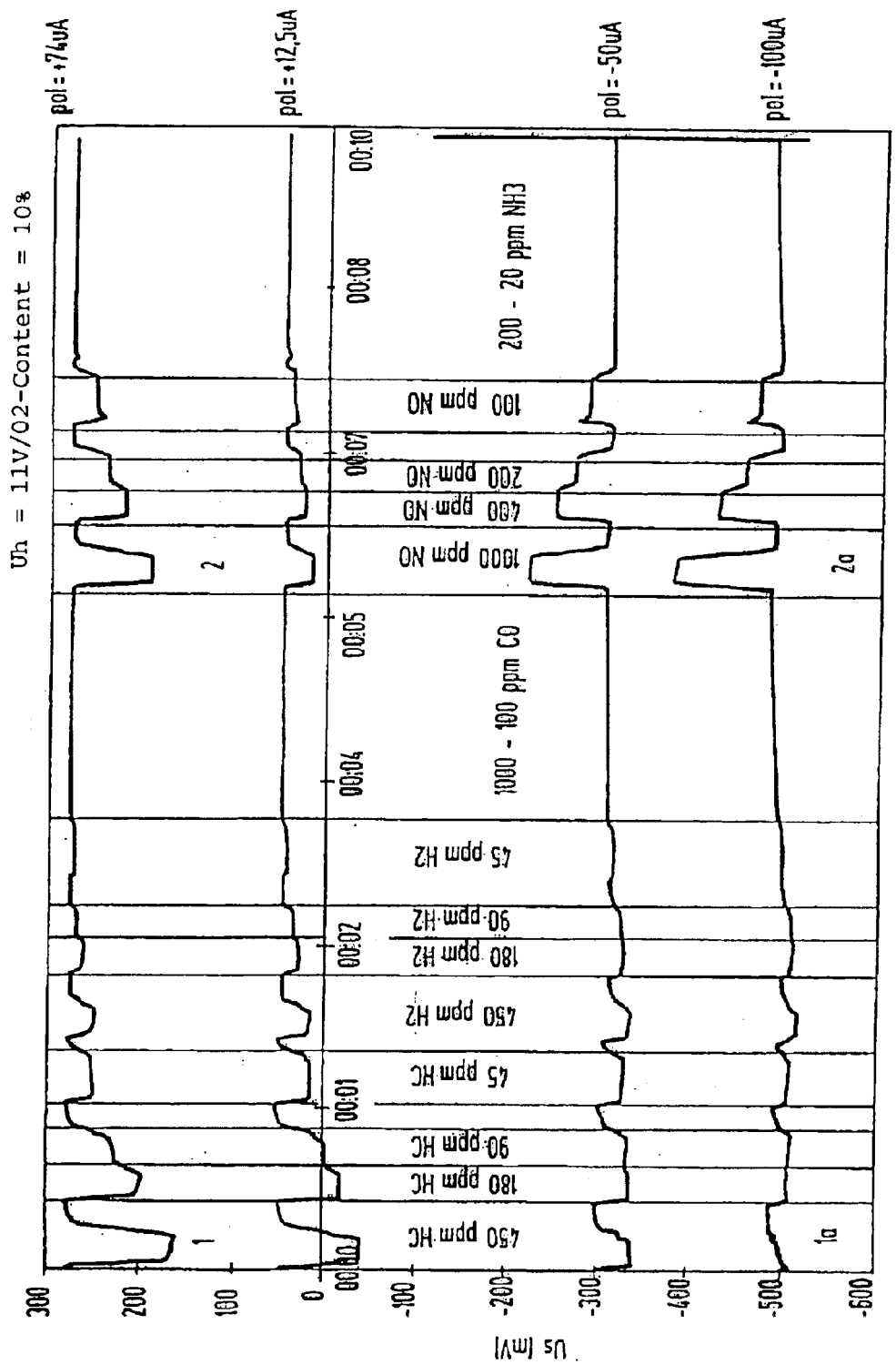
FIG. 2 shows the probe voltage, which is taken off at a polarized NOx mixed potential probe, as a function of time.

As an example, FIG. 2 shows the mixed potentials of hydrocarbons (450–45 ppm) (reference numeral 1) as well as the mixed potentials of nitrogen oxides (reference numeral 2). These mixed potentials are detected by means of a voltage-polarized current measurement (see FIG. 4) for a polarization voltage of +290 mV.

If the electrode is negatively polarized, then the signal amplitude of the hydrocarbon mixed-potential formations drops with increasing negative polarization (reference numeral 1a). The nitrogen oxide signal first drops with falling polarization voltage, reverses and then increases with increasing negative polarization voltage to 100 mV for a polarization voltage of −500 mV (reference numeral 2a).

Figure 3:
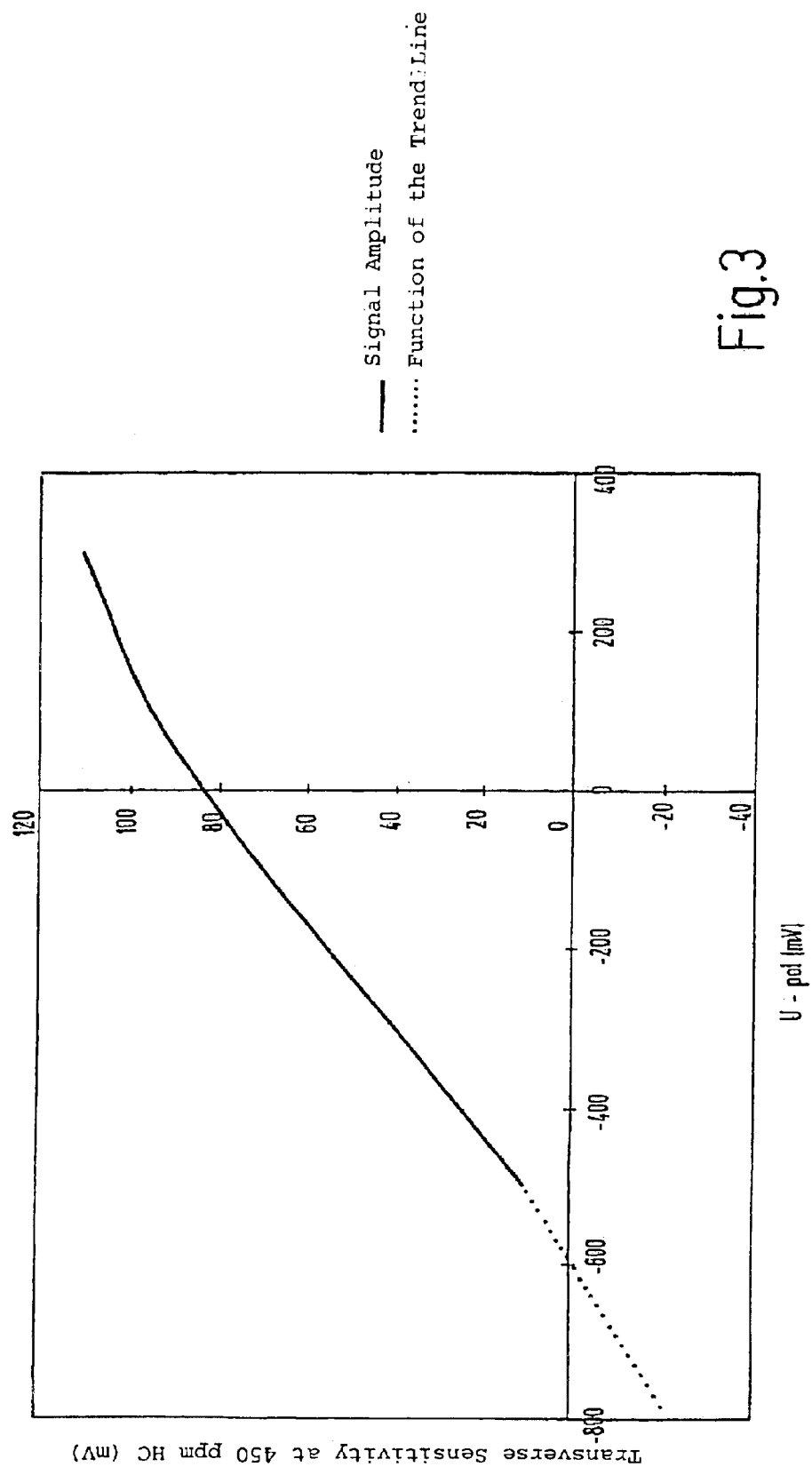
FIG. 3 shows the HC transverse sensitivity as a function of the pump voltage for a mixed potential exhaust-gas probe making use of the invention.

In FIG. 3, the amplitude of the hydrocarbon mixed-potential formations (transverse sensitivity) is plotted against the pump voltage or polarization voltage.

As shown in FIG. 3, no hydrocarbon transverse sensitivity is present for a pump voltage of −600 mV so that a measurement is possible of only the NOx component.

What is claimed is:

1. A circuit arrangement for carrying out a method for operating a mixed-potential exhaust-gas probe for an internal combustion engine wherein exhaust gas is generated, the exhaust-gas probe including: a heatable probe ceramic; a first electrode arranged in a chamber subjected to a reference atmosphere; and, a second electrode, which detects gas molecules, and is arranged in the exhaust gas of the internal combustion engine; the method comprising the steps of: providing a pump voltage source and applying a pump voltage across the first and second electrodes so that, in the interior of the chamber, a reduced oxygen partial pressure relative to the oxygen partial pressure in the exhaust gas is adjusted by the electrochemical pumping off of the oxygen molecules and the voltage across said first and second electrodes deviating from the thermodynamic equilibrium voltage of the reaction which takes place in said exhaust-gas probe; and, measuring and evaluating the current flowing across the electrodes; the arrangement comprising:

an inverting operational amplifier having a non-inverting input, an inverting input and a feedback loop;

a voltage divider R2 connected to said non-inverting input;

the exhaust-gas probe being connected to said inverting input;

a reference resistor R1 arranged in said feedback loop; and, a differential amplifier which amplifies the voltage difference between said non-inverting input and the output of the operational amplifier and outputs the difference as a measurement signal.

2. The circuit arrangement of claim 1, further comprising a switching device for switching the circuit arrangement for the voltage polarized current measurement over to the circuit arrangement for current polarized voltage measurement.

3. A circuit arrangement for carrying out a method for operating a mixed-potential exhaust-gas probe for an internal combustion engine wherein exhaust gas is generated, the exhaust-gas probe including: a heatable probe ceramic detecting gas molecules; a first electrode mounted in a chamber and the first electrode being subjected to a reference atmosphere; and, a second electrode arranged in the exhaust gas of the internal combustion engine; the method including the steps of: providing a pump voltage source and applying a pump voltage across the first and second electrodes so that a reduced oxygen partial pressure is adjusted relative to the oxygen partial pressure in the exhaust gas in the interior of the chamber by electrochemically pumping off the oxygen molecules; and, applying a constant current to the probe ceramic and measuring and evaluating the voltage which results between the first and second electrodes with this voltage deviating from the thermodynmic equilibrium voltage of the desired reaction which takes place in said exhaust-gas probe; the arrangement comprising:

a non-inverting operational amplifier having a non-inverting input, an inverting input and a feedback loop;

a voltage divider R2 connected to the non-inverting input;

a reference resistor R1 connected to the inverting input; said exhaust-gas probe being arranged in said feedback loop; and, a differential amplifier for amplifying the voltage difference at the sensor and outputting said voltage difference as a measurement signal.

4. The circuit arrangement of claim 3, further comprising a switching device for switching the circuit arrangement for the voltage polarized current measurement over to the circuit arrangement for current polarized voltage measurement.

* * * * *